US005494808A

United States Patent [19]

Fu

[11] Patent Number: 5,494,808
[45] Date of Patent: Feb. 27, 1996

[54] DEFINED MEDIUM OMPC FERMENTATION PROCESS

[75] Inventor: Jeffrey Fu, Hatfield, Pa.

[73] Assignee: Merck & Co., Inc., Rahway, N.J.

[21] Appl. No.: 332,195

[22] Filed: Oct. 31, 1994

Related U.S. Application Data

[63] Continuation-in-part of Ser. No. 307,971, Sep. 15, 1994, abandoned.

[51] Int. Cl.$^6$ .............................. C12N 1/20; C12P 21/00

[52] U.S. Cl. .................... 435/71.1; 435/101; 435/252.1; 435/253.6

[58] Field of Search .............................. 435/71.1, 252.1, 435/253.6, 101

[56] References Cited

U.S. PATENT DOCUMENTS

| | | | |
|---|---|---|---|
| 4,448,714 | 5/1984 | Cunliffe et al. | 435/71.3 |
| 4,465,669 | 8/1984 | Wissler et al. | 435/70.4 |
| 4,512,970 | 4/1985 | Wissler et al. | 530/350 |
| 4,588,692 | 5/1986 | Cunliffe et al. | 435/252.1 |
| 4,882,317 | 11/1989 | Marburg et al. | 514/54 |
| 5,045,456 | 9/1991 | Rienstra et al. | 435/101 |
| 5,314,811 | 5/1994 | Lee et al. | 435/101 |

FOREIGN PATENT DOCUMENTS

1750689A1 7/1992 U.S.S.R. .

OTHER PUBLICATIONS

D. Ikic et al Radori Imunoloskog Zauadq vol. 19–20 (1976–77) pp. 5–11.
B. Catlin J. Infectious Diseases 128(2): 178–194 1973.
I. Frantz, Jr. J. Bacteriology (73) pp. 757–761 1942.
K. Jyssum Acta Path 46(4):320–332 1959.
B. Anderson et al. Acta Path Micro Scand. Sect. B 86:275–281 1978.
L. LaScolea, Jr. et al Applied Micro 28(1):70–76 1974.

*Primary Examiner*—Herbert J. Lilling
*Attorney, Agent, or Firm*—Joanne M. Giesser; Jack L. Tribble

[57] ABSTRACT

A new fermentation process for the culture of *Neisseria meningitidis* incorporates a wholly synthetic medium and event based processing decisions. This process is capable of generating cells at production scale for the extraction and purification of outer membrane protein complex (OMPC) vesicles which are useful as a protein carrier for Pedvax-HIB® and pneumococcal conjugate vaccines.

7 Claims, 4 Drawing Sheets

DEFINED MEDIUM OMPC FERMENTATION PROCESS

This application is a continuation-in-part of U.S. application Ser. No. 08/307,971, filed Sep. 15, 1994 now abandoned.

BACKGROUND OF THE INVENTION

1. Field of the Invention

This patent disclosure is concerned with a new fermentation process for the culture of Neisseria meningitidis which incorporates a wholly synthetic medium and event based processing decisions. This process is capable of generating cells at production scale for the extraction and purification of any material which can be produced by culture of Neisseria meningitidis, and specifically, for isolation of an outer membrane protein complex (OMPC) which is useful, among other things, as a protein carrier for conjugate vaccines including PedvaxHIB® and pneumococcal conjugate vaccines.

2. Background of the Invention

The Outer Membrane Protein Complex (OMPC) of the bacterium *Neisseria meningitidis* has been used successfully as a protein carrier in a *Haemophilus influenza* type b (Hib) polysaccharide conjugate vaccine and a *Streptococcus pneumoniae* (Pn) polysaccharide conjugate vaccine to elicit anti-polysaccharide immune responses in young infants. These vaccines are produced by conjugating one, poorly immunogenic component (polysaccharide) with a second, strongly immunogenic component (OMPC). U.S. Pat. No. 4,695,624 described a method for preparing conjugates of poorly immunogenic bacterial polysaccharide and the strongly antigenic *Neisseria meningitidis* outer membrane protein complex (OMPC). Within the scope of that patent was a method for preparing a commercially available product, Pedvax-HIB®, which is a conjugate of OMPC and the capsular polysaccharide of *Haemophilus influenzae* type b.

Various methods are known for purifying OMPC from gram negative bacteria [Frasch et al., *J, Exp. Med.* 140, 87 (1974); Frasch et al., *J. Exp, Med.* 147, 629 (1978); Zollinger et al., U.S. Pat. No. 4,707,543 (1987); Helting et al., *Acta Path. Microbio. Scand. Sect. C* 89, 69 (1981 ); Helting et al., U.S. Pat. No. 4,271,147; Frasch et al., U.S. Pat. No. 4,601, 903; and Vandevelde et al., U.S. Pat. No. 4,451,446]. One method for preparing OMPC, described by Helting et al., in U.S. Pat. No. 4,271,147, comprised detergent extraction of the OMPC of *Neisseria meningitidis* cells grown in culture, followed by purification of the OMPC. According to the Helting scheme, purification of OMPC is achieved by repeated ultracentrifugation steps and/or ethanol precipitation. Any of these known methods for purification of OMPC are applicable to the *Neisseria meningitidis* cells produced according to the instant patent disclosure for use in production of conjugate vaccines. However, fermentation methods which provide an inconsistent material from which the OMPC is to be extracted negatively impacts on all of the foregoing OMPC extraction/purification schemes. An efficient and consistent method for commercial scale fermentation of *Neisseria meningitidis* for production of OMPC has been lacking.

The OMPC carrier is derived by detergent extraction of whole cells. Thus, the consistent generation of suitable biomass is central to an effective OMPC production process. Existing processes for culturing Neisseria employ complex media for fermentation and time associated criteria for batch termination. Serious faults which negatively impact on product yield and quality occur in the known fermentation processes. These processes are at the mercy of lot to lot variation in the quality of complex components in the feed stocks (for example, in the quality of yeast extract); time based process decisions are prone to error due to the stochastic nature of biological systems. These inconsistencies in processing are exacerbated in combination with variations in complex media.

It is widely accepted that the cGMP (U.S. FDA current good manufacturing practice) manufacture of complex biological therapeutics and vaccines must be controlled at all stages of the production process and that final release testing is not itself sufficient to guarantee quality, safety, and efficacy of the final product (FDA Title 21, Code of Federal Regulations, Parts 210, 211, and 600–680). Process validation ensures that the manufacturing operations perform as intended within established specifications. Implicit in this definition is that any given process is well defined and reproducible. Conventional Neisseria fermentation processes rely on chemically undefined or complex media components to speed development time and facilitate robust cultivation, sometimes at the expense of a basic understanding of cell metabolism and strict in-process control. Due to the very nature of complex media components, release testing might not discriminate effectively among lots of complex media; for this reason, the ability to consistently procure a proven grade of complex raw material for fermentation is time consuming and may not always be possible.

Several criteria are central to medium development for microbial fermentation as applied to cGMP biologics production. Ideally, the medium should contain only essential components, be easily prepared in a reproducible manner, and support robust high-cell density culture. A chemically defined medium is inherently more reproducible than a complex medium. Furthermore, a chemically defined medium enables discrete analysis of the effect of each component and strict control of medium formulation through identity and purity testing of raw materials. Finally, the fermentation medium should support the cultivation of the microorganism in question to high-cell density to improve volumetric productivity and to generate a final culture whose composition and physiological condition is suitable for downstream processing. To date, a chemically defined medium and fermentation process for reproducible, high-density cultivation of Neisseria has not been available. Catlin [*J. Inf. Dis.* 128:178–194, 1973], (hereinafter referred to as "Catlin"), who was principally interested in developing a taxonomy of Neisseria strains based on nutritional requirements rather than large scale fermentation, described a complex chemically defined medium named NEDF, containing approximately 54 ingredients, including all twenty naturally occurring amino acids, for growth of Neisseria. In addition, Catlin described a medium called MCDA containing 18 ingredients (in mM: NaCl, 100; KCL, 2.5; $NH_4Cl$, 7.5; $Na_2HPO_4$, 7.5; $KH_2PO_4$, 1.25; $Na_3C_6H_5O_7.2H_2O$, 2.2; $MgSO_4.7H_2O$, 2.5; $MnSO_4.H_2O$, 0.0075; L-glutamic acid, 8.0; L-arginine.HCl, 0.5; glycine, 2.0; L-serine, 0.2; L-cysteine $HCl.H_2O$, 0.06; sodium lactate, 6.25 mg of 60% syrup/mLof medium; glycerin, 0.5% (v/v); washed purified agar, 1% (wt/vol) $CaCl_2.2H_2O$, 0.25; $Fe_2(SO_4)_3$, 0.01 ) which was reported to support growth of *Neisseria meningitidis* on agar. The ability of MCDA to support growth in liquid medium (that is absent addition of agar) was not reported.

La Scolea et al., [*Applied Microbiology* 28:70–76, 1974] who like Catlin (see above) was also interested in defining the nutritional requirements of Neisseria strains, reported on the development of a defined minimal medium named GGM for the growth of *Neisseria gonorrhoeae*. The medium contained minimal salts, eight amino acids, two nitrogen bases, vitamins, coenzymes, metabolic intermediates and miscellaneous components. La Scolea et al., reported growth of this strain to an optical density of 400 Klett units. An absorbance of 1 at 600 nm is considered equivalent to 500 Klett units [see Gerhardt et al., *Manual of Methods for General Bacteriology*, 1981, ASM., p. 197]. Therefore, the maximum reported growth density achieved by LaScolea et al., was less than about one (1) absorbance unit.

SU 1750689 A1 described a method for preparing polysaccharide-protein vaccines against *Neisseria meningitidis* B. A defined medium was described having the following composition, g/L:

| | |
|---|---|
| Sodium L-glutamate | 1.30 ± 0.10 |
| L-cysteine hydrochloride | 0.03 ± 0.01 |
| Potassium chloride | 0.09 ± 0.01 |
| Sodium chloride | 6.00 ± 1.00 |
| Magnesium sulfate heptahydrate | 0.06 ± 0.01 |
| Ammonium chloride | 1.25 ± 0.01 |
| Disubstituted sodium phosphate dodecahydrate | 2.50 ± 0.20 |
| Trisubstituted sodium citrate | 0.50 ± 0.10 |
| Glucose | 1.60 ± 0.20 |

In this medium, it is reported that Neisseria may be cultured to a final optical density of 1.5±0.2 on the FEK-56M scale. This is an unfamiliar scale for optical density determination. However, based on the available carbon sources in the above noted medium, it is predictable that the maximum absorbance achievable would be in the range of about 1.5 absorbance units.

In this patent disclosure, we describe a large-scale, high-cell density (5 g/L dry cell weight, and an optical density of between about 10–13 at 600 nm) fermentation process for the cultivation of *N. meningitidis*. Since current requirements for the production of human biologics mandate strict control of all aspects of the manufacturing process, several key features of the process, including a chemically defined medium and a rational, event-based harvest criterion, support current good manufacturing practice (cGMP) and increased productivity.

SUMMARY OF THE INVENTION

The defined medium of this invention (MC.6) for culture of *Neisseria meningitidis* contains only salts, 5 amino acids, and a carbon source. In one optimized formulation, the medium contains (±10%) the following components (mg/L) and supports the efficient and reproducible growth of *Neisseria meningitidis* for isolation of OMPC or other biomass obtainable from cultured *Neisseria meningitidis*:

| Component | MC.6 |
|---|---|
| NaCl | 5800 |
| $K_2HPO_4$ | 4000 |
| $NH_4Cl$ | 1000 |
| $K_2SO_4$ | 1000 |
| Glucose | 10000 |
| L-Glutamic Acid | 3900 |
| L-Arginine | 150 |
| Glycine | 250 |
| L-Serine | 500 |
| L-Cysteine.HCl | 100 |
| $MgCl_2.6H_2O$ | 400 |

-continued

| Component | MC.6 |
|---|---|
| $CaCl_2.2H_2O$ | 28 |
| Fe(III) Citrate | 40 |

The process of this invention comprises culturing *Neisseria meningitidis* cells in MC.6 and harvesting the cells in late log, early stationary phase.

BRIEF DESCRIPTION OF THE DRAWINGS

FIG. 1. Growth profile of *N. meningitidis* in MC.6 defined medium in a 250-L production fermenter. FIG. 2(*a*) A series of optical density curves obtained from three independent experiments (runs 1, 2, and 3) demonstrate growth rate and final cell yield consistency in MC.6 medium. FIG. 1(*b*) Culture viability is based on the relative change in the number of total (particle) cell counts compared to viable (CFU/mL) cell counts (data from run 1 ).

FIG. 2. Growth ($OD_{600}$) and glucose utilization of *N. meningitidis* in Catlin medium. The fermentation was carried out in a 16-L fermenter (New Brunswick Scientific) under similar conditions described in the experimental protocol for the 250-L production fermentation. Complete Catlin medium was purchased from Gibco BRL and filter sterilized (0.22 μm).

FIG. 3. On-line and off-line analyses of the *N. meningitidis* MC.6 defined medium fermentation in the 250-L production fermenter FIG. 3(*a*) CER, OUR, and RQ were calculated from on-line measurements of $CO_2$ and $O_2$ exhaust gas concentrations; the batch was discontinued at the predetermined harvest point based on a decrease in successive CER or OUR values (data from run 2). The following metabolites were analyzed off-line during the time course (data from run 3) to determine: FIG. 3(*b*) glucose utilization and acetate accumulation; FIG. 3(*c*) amino acid utilization and overflow of aspartic acid and alanine; and FIG. 3(*d*) extracellular cation composition.

| ABBREVIATIONS: | |
|---|---|
| OMPC = | *Neisseria meningitidis* B11 Outer Membrane Protein Complex |
| cGMP = | current good manufacturing practice |
| FDA = | U.S. Food and Drug Administration |
| $OD_{600}$ = | optical density at 600 nm |
| CFU = | colony forming units |
| $t_d$ = | culture doubling time ($hour^{-1}$) |
| CER = | carbon dioxide evolution rate (mmol/L/hr) |
| OUR = | oxygen consumption rate (mmol/L/hr) |
| RQ = | respiratory quotient (CER/OUR) |
| TCA = | tricarboxylic acid |
| HEPES = | N-[2-hydroxyethyl]piperazine-N'-[2-ethane-sulfonic acid] |
| NIH BL-2-LS = | National Institutes of Health, biosafety level 2, large-scale |
| RPM = | revolutions per minute |
| PBS = | phosphate buffered saline, pH 7 |
| Glu = | L-glutamic acid |
| Ala = | L-alanine |
| Arg = | L-arginine |
| Asp = | L-aspartic acid |
| Gly = | glycine |
| Ser = | L-serine |
| Hib = | *Haemophilus influenza* type b |
| Pn = | *Streptococcus pneumoniae* |
| Ps = | capsular polysaccharides |

DETAILED DESCRIPTION OF THE INVENTION

Figure 1A:
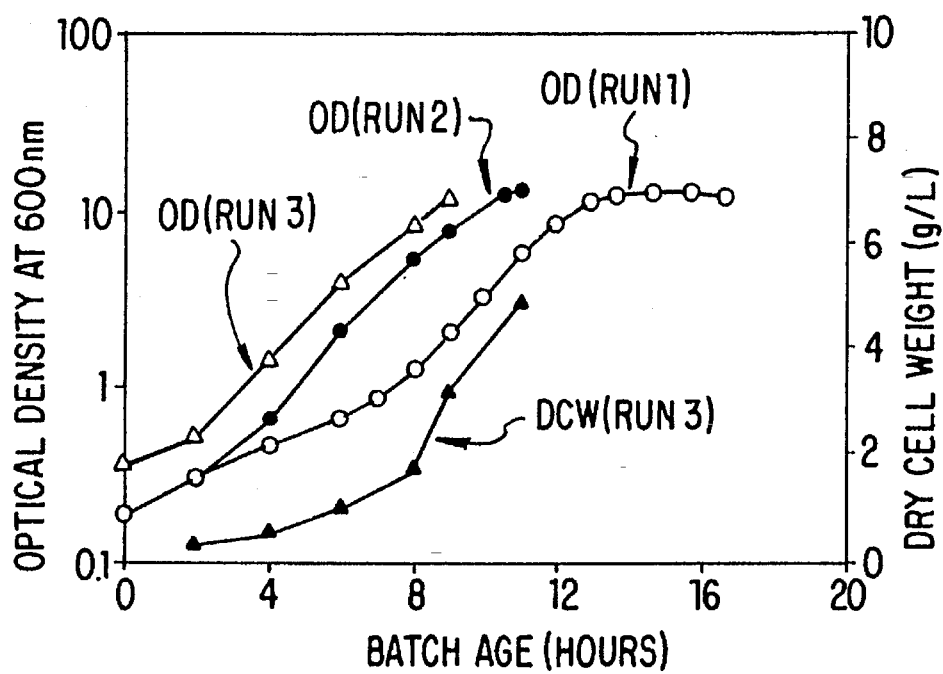

1. Defined Medium Development:

The chemically defined medium disclosed herein and designated MC.6, was developed by deleting components from the well-established, but multi-component (>50) Neisseria defined medium described by Catlin [J. Inf. Dis. 128:178–194, 1973]. The defined medium was evaluated by growth promotion testing on agar solid-substrate, in shake-flask culture, and in fermenters. Once we determined the minimal required nutrients, we rebalanced the individual medium component concentrations to support high-cell density cultivation of *N. meningitidis*. We confirmed that providing only 5 amino acids (Glu, Ser, Gly, Cys, Arg) in addition to an array of salts and glucose generates robust growth in liquid media. We were able to sequentially propagate this culture on a solid substrate containing the MC.6 medium background without any of the amino acid components in a 5% $CO_2$ enriched environment; however, growth was not observed consistently in liquid culture (even in the presence of 5% $CO_2$) without the amino acid components being present. This observation is consistent with the report of Jyssum, K [*ACTA Path* 46:320–332, 1959]. In order to adapt Neisseria to increase growth in liquid media, several passages of the bacterium on solid media is helpful.

Surprisingly, we have discovered that although we eliminated multiple components from the medium described by Catlin, through appropriate balancing of the retained components, we were able to achieve a greater cell density than that reported by Catlin by a factor of about two-fold. We confirmed this result by growing Neisseria under similar conditions in both media (see FIGS. 1 and 2). In one particular embodiment of this invention, the medium has the following composition (±10% for each component):

| Component | MC.6 |
| --- | --- |
| NaCl | 5800 |
| $K_2HPO_4$ | 4000 |
| $NH_4Cl$ | 1000 |
| $K_2SO_4$ | 1000 |
| Glucose | 10000 |
| L-Glutamic Acid | 3900 |
| L-Arginine | 150 |
| Glycine | 250 |
| L-Serine | 500 |
| L-Cysteine.HCl | 100 |
| $MgCl_2.6H_2O$ | 400 |
| $CaCl_2.2H_2O$ | 28 |
| Fe(III) Citrate | 40 |

Naturally, media containing these elements but in slightly different proportions would be obvious variants of this invention. For example, any of these components may be increased or decreased by about 10% without substantially affecting *Neisseria meningitidis* fermentation efficiency. That is, we have defined medium components that are both necessary and sufficient for achieving high-density growth of *Neisseria meningitidis*.

It is obvious to those skilled in the art that the improved process and medium disclosed herein could be applied to obtaining any product which may be harvested from *N. meningitidis* biomass. Furthermore, the methods and medium disclosed herein could be used to grow related micro-organisms such as *N. gonorrhoeae*, and even such divergent bacteria as *E. coli*, provided that appropriate rebalancing of the medium components and harvest criteria are defined by routine experiment based on the disclosure found herein.

2. Seed Train:

The seed train for a fermentation process should be as straightforward and condensed as possible in order to minimize cultivation time and risk of contamination. However, some physiological constraints must be considered for the cultivation of Neisseria. A stimulatory level of dissolved $CO_2$ significantly decreases the lag phase of growth as reported by Morse et al., [*The Gonococcus,* 213–253, R. B. Roberts (Ed.), Wiley, New York, 1977], especially for cultures inoculated from a static source (e.g., frozen seed culture). Furthermore, it has been observed by Jyssum, K., [*ACTA Path* 46:320–332, 1959], that the seeding density of a newly inoculated culture is also a strong determinant for establishing culture growth, especially in minimal defined medium. Thus, we determined the inoculation volume and cell density at seed transfer stages based on the above considerations.

We developed a seed train leading to a 250-L scale fermentation which comprises successive culture of the frozen seed in a 250-mL flask, a 2-L flask, and a 15-L seed fermenter. One extra 250-mL and 2-L flask is routinely employed to monitor growth of the culture without risk of contamination. A 5% $CO_2$/air environment is used in the initial 250-mL seed stage to minimize the growth lag from the frozen inoculum culture source (2% transfer). All other fermentation stages were carried out in air. A constant 5% transfer volume and a cell density transfer range of $OD_{600}$= 1–2 for the remaining culture stages reproducibly allow rapid growth upon transfer without enhanced $CO_2$ tension. Scale-up of this process is achieved simply by either increasing the working volumes of each culture stage or by adding additional seed propagation stages while maintaining the same inocula transfer volumes.

For a defined medium process, it is advantageous to have (1) a defined seed medium, including the medium used to generate the seed source, and (2) a seed medium that is similar in composition to the production fermenter defined medium. With this practice, the fermentation is free of complex component contamination which may alter the consistency of an otherwise well-defined process. Moreover, the composition of the production medium may be altered significantly by the introduction of foreign nutrients from a complex seed medium, or the concentration of a key substrate in the production medium may be substantially increased as a consequence of seed medium carryover, whether from a complex or defined medium source. In a preferred embodiment of this invention, the same defined medium is used for the seed stages and the production stage except that the flask seed medium is buffered (100 mM HEPES or a similar buffer) in order to maintain constant pH at 7. The buffer is diluted by about 400-fold in the production fermenter, where pH is principally controlled by on-line measurement of pH with alkali and acid addition as need. The frozen culture source is also preferably generated in the same defined medium.

Figure 1B:
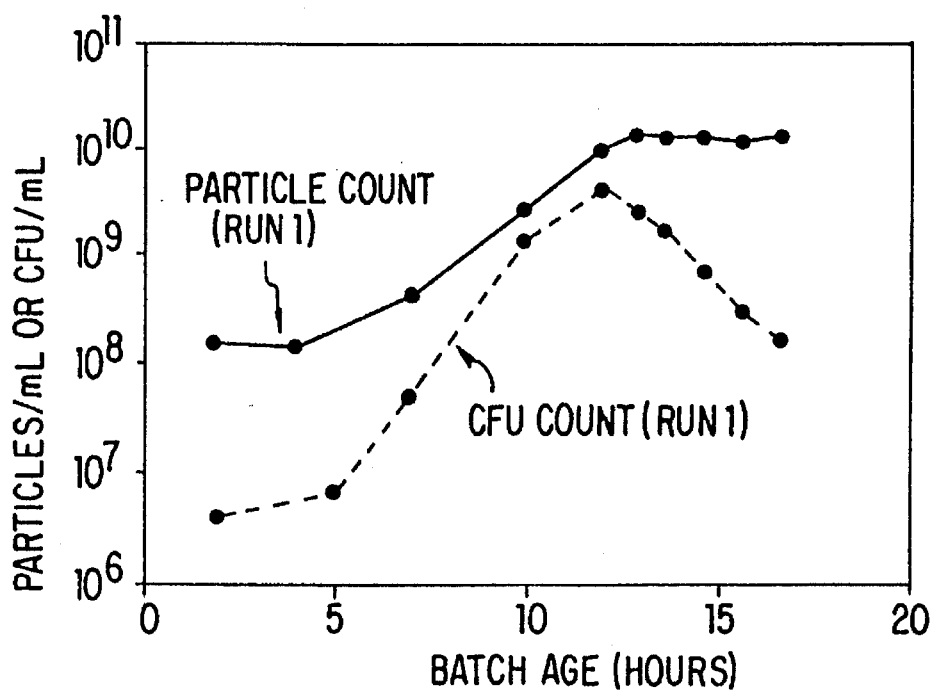
Figure 2:
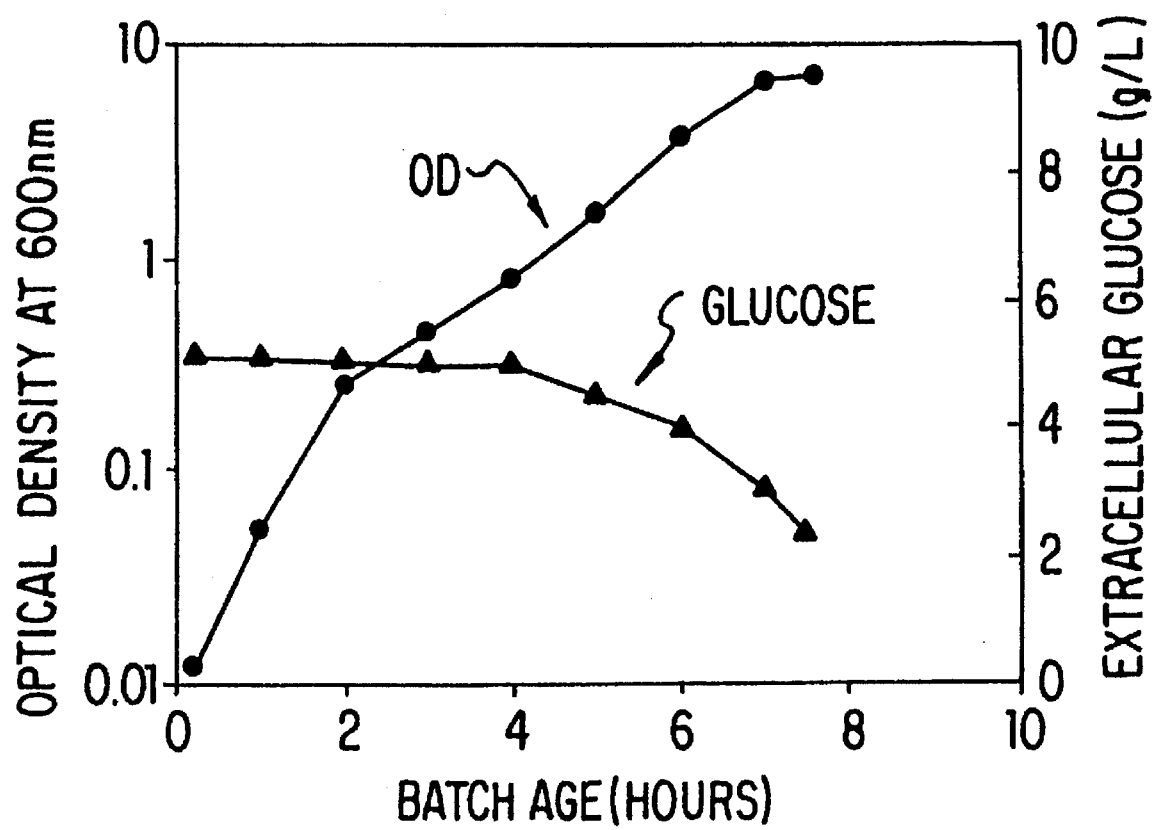
Figure 3B:
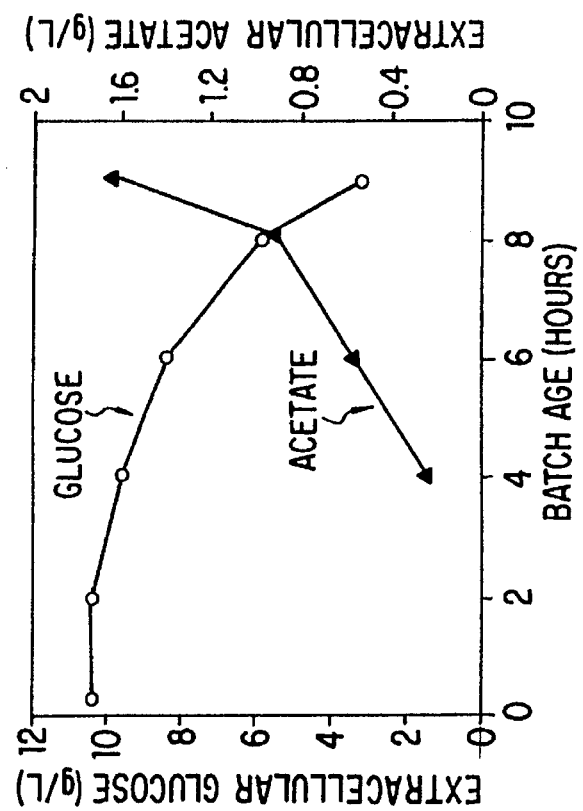
Figure 3A:
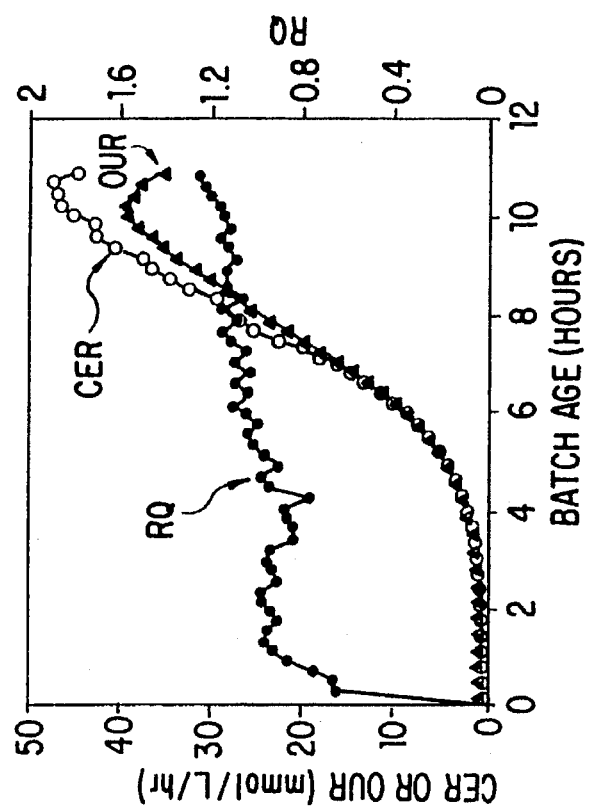
Figure 3D:
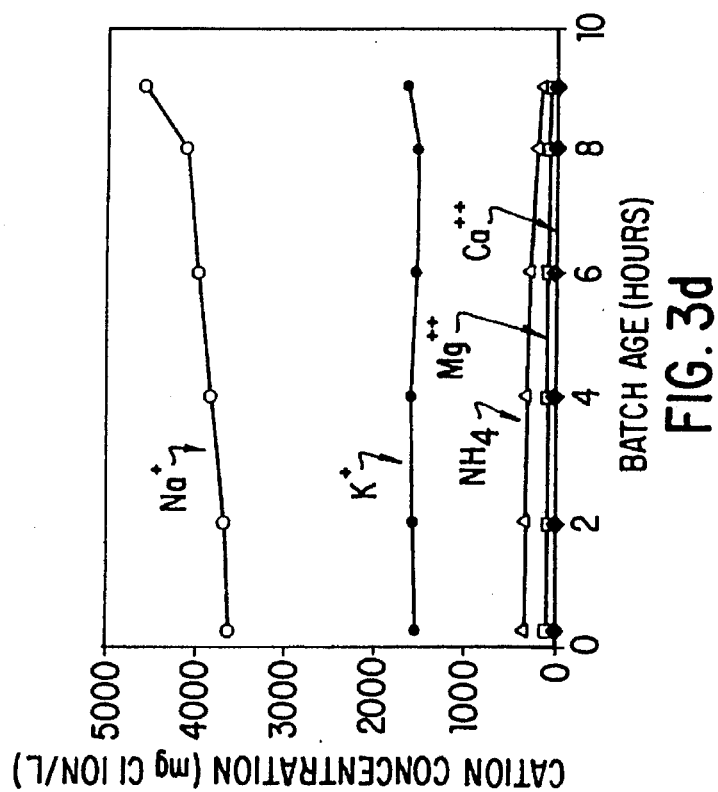
Figure 3C:
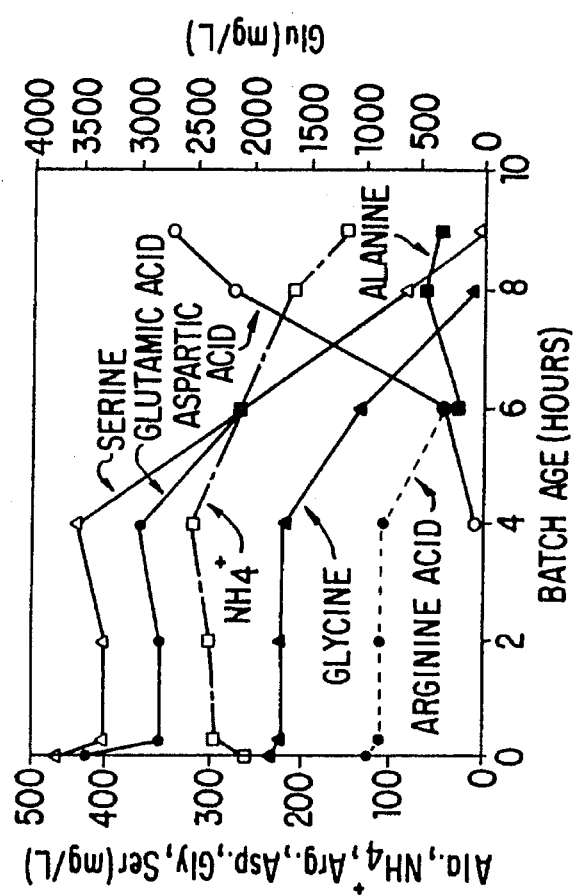

3. Production Fermentation:

A typical growth profile for *N. meningitidis* in MC.6 in the production fermenter is characterized by exponential growth, without a detectable lag phase, followed by stationary and death phases. A series of growth curves depict culture growth based on optical density, dry cell weight, particle (i.e., total) counts, and colony forming cell counts (FIG. 1). Under controlled cultivation conditions employing MC.6 medium, growth in the production vessel is consistent (FIG. 1a) with a characteristic doubling time of approximately 1.5 hours and a surprisingly high final cell yield of approximately 5 g/L dry cell weight ($1-2\times10^{10}$ cells/mL)

during balanced growth. A similar growth profile is obtained in the much more complex, widely used medium of Catlin (FIG. 2). However, the final cell yield in the Catlin medium is approximately half that obtained in the MC.6 medium under similar cultivation conditions. Glucose did not limit final cell yield in either fermentation. The MC.6 medium supported elevated growth levels while eliminating numerous nutrients from the Catlin formulation. This offers cost savings and simplicity for industrial applications. As might be expected, the doubling time during balanced growth of $N.$ $meningitidis$ B11 in the MC.6 medium ($t_d$=1.5 hour) was somewhat longer than that observed in the richer Catlin medium ($t_d$=1 hour).

Since the protein carrier used in conjugate vaccines is an outer membrane extract of whole $N.$ $meningitidis$ cells, increased biomass plays a central role in increasing the productivity of the fermentation process. However, in the case of pathogenic Neisseria species, the composition, and thus extraction and isolation properties, of the outer membrane is dynamic and is strongly dependent on culture conditions and cell physiology [see Chen et al., $Clin,$ $Microbiol.$ $Rev.$ 2:S35–S40, 1989; see also Frasch et al., $J.$ $Bacteriol.$ 127:973–981, 1976]. More specifically, changes in lipooligosaccharide chain length [see Schneider et al., $Inf.$ $and$ $Immun.$ 45:544–549, 1984] and outer membrane protein composition [see Arakere et al., $J.$ $Bacteriol.$ 175:3664–3668, 1931] have been identified during the transition from exponential to stationary phase culture. Furthermore, we have identified a rapid decay in the viable (CFU/mL) cell count immediately following the exponential growth phase (FIG. 1$b$).

In addition to the MC.6 medium, we have discovered in laboratory-scale OMPC isolations from cultures harvested during late-exponential or late-stationary phase growths (from the experiment described in FIG. 1$b$), that there is about a 2-fold difference in final OMPC yield based on protein content at the final purification step. Thus, according to the method of this invention, harvest of actively growing, late-exponential phase cells which exhibit a higher cell CFU/mL count is preferred. To accomplish this, we optimized the batch harvest age for the production fermentation of OMPC by maximizing biomass and viable cell concentration (based on CFU/mL) by harvesting the Neisseria culture at the transition point from exponential- to stationary-phase growth. We rapidly and non-invasively detect a clear and abrupt change in the $CO_2$ and $O_2$ off-gas concentrations [expressed in terms of carbon dioxide evolution rate (CER) and oxygen consumption rate (OUR)] by mass spectrometry at this growth transition point (FIG. 3$a$). Fermentation broth harvest is triggered by a decrease in successive CER and OUR time points using a 10 minute sampling interval. This approach establishes a rational event-based criterion for harvest of the fermentation broth which, in this case, provides greater in-process control than a more traditional, time-based procedure. For example, variations in total batch age of the production fermentations described in FIG. 1$a$ naturally occur because of slight differences in seeding density, despite tight control over seed transfer conditions. A harvest based strictly on a fixed time interval after inoculation of the fermenter does not have the advantages described above and produces greatly varying cell and OMPC isolation yields. Furthermore, the event-based harvest described herein offsets inoculation effects and consistently allows maximum cell and OMPC yields.

Consistent with cGMP in-process control, the production fermentation and the seed fermentations described herein can be characterized for growth and consistency by on-line and off-line analyses. The culture of $N.$ $meningitidis$, under the conditions described, exhibits a respiratory quotient (RQ) of 1.0–1.2 (FIG. 3$a$). The extracellular glucose and amino acid profiles also serve to define substrate utilization during the fermentation (FIG. 3$b$–$d$). In this medium, growth is amino nitrogen limited, and glucose is in excess at the time of optimized cell harvest. However, simple amino acid supplementation to the MC.6 base medium, added either to the initial batch formulation or as a shot addition during mid-exponential growth, in dissolved oxygen controlled fermenters, did not result in a commensurate cell yield increase. Measurements of sodium, ammonium, potassium, magnesium, and calcium ion content indicate that these cations were not limiting during fermentation (FIG. 3$d$). Ferric ion could not be detected by this method; however, shake-flask experiments indicated that increasing ferric citrate concentrations in MC.6 medium did not support additional growth. Accumulation of acetate (FIG. 3$b$), aspartic acid, and alanine (FIG. 3$d$) as metabolic by-products ensues mid-way into the batch cycle. A carbon material balance is presented in Table 1, which identifies the outcome of carbon metabolism from inoculation of the production culture to late-exponential growth phase at the time of harvest. These data points account for approximately 95% of the carbon flow in the system.

TABLE 1

Carbon material balance for a typical $N.$ $meningitidis$ B11 production fermentation in MC.6 medium. This analysis demonstrates the accountability of major organic carbon derived from the nutrients and its outcome in the form of biomass and metabolic by-products. The comparison was made between the time points immediately after inoculation of the fermenter and the time of optimal harvest (late exponential growth phase) as determined by off-gas analysis. All values were derived from direct measurements (data from FIG. 3) and correlated to equivalent carbon content based on molecular composition, unless otherwise stated. The carbon derived from Fe(III)·citrate was omitted due its low concentration in the medium (<1 mM carbon) and because it was unclear whether $N.$ $meningitidis$ can utilize the citrate that was complexed with $Fe^{3+}$. Due to lack of an assay, it was assumed that all of the cysteine was exhausted by the time of harvest. The starting cysteine carbon content was 1.92 mM:

| Carbon Conc. (mM) | Molecular Conc. (mM) | Component |
|---|---|---|
| I. Carbon derived from nutrients (immediately after fermenter inoculation) | | |
| 337 | 56.2 | Glucose |
| 120 | 24.0 | L-Glutamic acid |
| 4.42 | 0.737 | L-Arginine |
| 13.5 | 4.50 | L-Serine |
| 2.48 | 0.827 | L-Cysteine (formulated value) |
| 6.32 | 3.16 | Glycine |
| 1.43 | n/a | Biomass ($OD_{600}$/DCW correlation) |
| total 485 | | % carbon = 39.1% of DCW |
| II. Carbon distribution at the time of harvest | | |
| 108 | 18.0 | Residual glucose |
| 140 | 140 | Total $CO_2$, evolved |
| 10.5 | 2.63 | L-Aspartic acid, excreted |
| 1.58 | 0.527 | L-Alanine, excreted |
| 54.5 | 27.2 | Acetic acid, excreted |
| 146 | n/a | Biomass ($OD_{600}$/DCW correlation) |
| total 461 | | |
| III. Summary | | |
| Net glucose utilized | | 38.2 mM glucose |
| Total $CO_2$ evolved | | 140 mM $CO_2$ |

TABLE 1-continued

| | |
|---|---|
| Acetate excreted | 27.2 mM |
| Net biomass produced | 145 mM carbon equivalent |

Both complex and defined media have been developed over the years for the cultivation of N. meningitidis and the closely related species N. gonorrhoeae [ Mueller et al., P.S,E.B,M. 48:330–333, 1941; Tryptic soy broth, Difco Manual, Tenth E.d,:1027–1028, Difco Laboratories, Detroit, Mich., 1984; Frantz, I.D., J. Bacteriol. 73:757–761, 1942; Port et al., Can. J. Microbiol. 30:1453–1457, 1984; LaScolea, et al., Appl. Microbiol. 28:70–76, 1974; Andersen et al., Acta Path. Microbiol. Scand. 86:275–281, 1978]. However, effective large-scale fermentation of this pathogen for biologics production necessitates a cultivation medium which offers high cell and product yields, reproducibility, ease and economy of preparation, and low levels of other substances (e.g., pyrogens and particulates). A survey of results reported in known media indicates that, at best, the final cell yields in either the complex or defined media were two-fold lower than the results we obtain with the MC.6 medium described herein. Minimal chemically defined medium helps to ensure greater interlot fermentation consistency and decreases preparation cost and time. An increasingly important aspect of biologics manufacturing is the implementation of a defined medium so that individual components can be analyzed for chemical purity and identity.

Metabolic aspects of the fermentation process of this invention are well defined by a characteristic RQ and a carbon material balance with 95% closure which provided key insight into carbon catabolism. In pathogenic Neisseria species, glucose is catabolized by the Entner-Doudoroff and pentose phosphate pathways, and the only detectable non-gaseous end product of glucose metabolism is acetate [Morse et al., J. Bacteriol. 120:702–714, 1974]. Activity of the complete Embden-Meyerhof-Parnas pathway has not been observed. The low level of acetate accumulation in the medium (FIG. 3b) during exponential growth was consistent with a dominant contribution of glucose catabolism through triose phosphate cycling of the pentose phosphate pathway which generates 6 $CO_2$ equivalents per glucose without the formation of pyruvate. Extracellular formate, pyruvate, succinate, and lactate were not detected. Metabolic studies indicate that pyruvate is stoichiometrically oxidized to acetate since the TCA cycle is only partially functional in pathogenic Neisseria species during glucose metabolism [Morse et al., The Gonococcus, R. B. Roberts (Ed.), Wiley, New York: 213–253, 1977]. The major participation of the pentose phosphate pathway, deduced from minimal acetate overflow, has not been reported in the literature, presumably due to the heavy reliance on rich defined or complex media for radiorespirometric studies. Increased levels of acetate accumulation (up to 5 fold) have been observed for this strain when cultivated in a medium similar to MC.6 but which included a yeast extract supplement. Therefore, carbon utilization according to the instant process is more efficiently converted into biomass. The characteristic RQ of approximately 1.0 in MC.6 medium is consistent with the oxidation of glucose by both pathways, although catabolism of the amino acids in this medium complicates this interpretation. The excretion of aspartic acid and alanine detected midway during the batch cycle (FIG. 3d) may be associated with glutamic acid transamination reactions generating α-ketoglutarate which can feed the energy generating part of the TCA cycle reactions to malate [see Morse et al., The Gonococcus, R. B. Roberts (Ed.), Wiley, New York: 213–253, 1977].

The N. meningitidis fermentation process of this invention for the production of OMPC is amenable to strict in-process controls which are consistent with cGMP. In addition to defined medium, several other control features of the instant method improve consistency of fermentation. These include a novel, direct frozen seed inoculation into liquid medium to quantitatively initiate the seed train. A more traditional Neisseria seed train requires an intermediate solid substrate step to accumulate biomass [see for example LaScolea et al., Appl. Microbiol. 28:70–76, 1974], which is strongly dependent on operator technique and, in an industrial application, could lead to broad variations in the starting seed density affecting the culture lag phase and seed stage timing. Seed flask medium is strongly buffered to maintain constant pH and seed cultures are transferred following a narrow $OD_{600}$ range. Batch age in the production termenter is monitored non-invasively by mass spectrometry of the fermenter exhaust gas. At the end of exponential growth, the precise time of harvest is triggered based on a physiologically relevant parameter (decline in OUR or CER) and provides a tightly controlled mechanism to deliver consistent starting material for OMPC extraction. These strict in-process controls, in combination with a chemically defined medium, help to maximize OMPC productivity and minimize interlot variation to fulfill industrial demands for efficient processing and cGMP compliance.

From the foregoing description of the invention and the Examples that follow, the embodiments of this invention include, but are not limited to:

A defined medium, named MC.6, which comprises, (±10%) the following components (mg/L):

| Component | MC.6 |
|---|---|
| NaCl | 5800 |
| $K_2HPO_4$ | 4000 |
| $NH_4Cl$ | 1000 |
| $K_2SO_4$ | 1000 |
| Glucose | 10000 |
| L-Glutamic Acid | 3900 |
| L-Arginine | 150 |
| Glycine | 250 |
| L-Serine | 500 |
| L-Cysteine.HCl | 100 |
| $MgCl_2.6H_2O$ | 400 |
| $CaCl_2.2H_2O$ | 28 |
| Fe(III) Citrate | 40 |

The use of MC.6 for fermentation of Neisseria meningitidis to support the efficient and reproducible growth of Neisseria meningitidis for isolation of biomass, including OMPC.

A method for culturing Neisseria meningitidis cells to an optical density of about 10–13 at 600 nm, which comprises culturing *Neisseria meningitidis* cells in a medium containing only the five amino acids Glu, Arg, Gly, Ser and Cys, salts and a carbon source, and harvesting the cells in late log or early stationary phase. This method may further comprise the steps of:

(a) preparing a frozen seed inoculum of *Neisseria meningitidis* in a medium containing only the five amino acids Gly, Arg, Gly, Ser and Cys, salts, a carbon source, buffered to maintain a pH of about 7, and a cryoprotective agent;

(b) preparing a seed inoculum in the same medium used in Step(a) but buffered to maintain a pH of about 7, using about a 1/100th volume of the frozen seed inoculum of Step(a) to initiate growth, and growing the *Neisseria meningitidis* to an optical density at 600 nm of about 1–2 in an atmosphere of about 5% $CO_2$;

(c) transferring the seed inoculum of Step(b) into a volume of the same medium used in Step(b) equal to about 10–100 fold the volume of the seed inoculum and growing this culture to an optical density of about 1–2 at 600 nm;

(d) inoculating a fermentation vessel containing about 10–100 fold the volume of the same medium as in the culture of Step 9(c), without addition of buffer, and culturing the *Neisseria meningitidis* with addition of acid or base as needed to maintain the pH at about 7, and supplying sufficient dissolved oxygen to maintain exponential growth as measured by carbon dioxide evolution rate (CER) and oxygen uptake rate (OUR);

(e) optionally, inoculating a fermentation vessel containing about 10–100 fold the volume of the same medium as in the culture of Step 9(c), without addition of buffer, and culturing the *Neisseria meningitidis* with addition of acid or base as needed to maintain the pH at about 7, and supplying sufficient dissolved oxygen to maintain exponential growth as measured by carbon dioxide evolution rate (CER) and oxygen uptake rate (OUR); and (f) harvesting the *Neisseria meningitidis* of Step(d) at the point where the CER and OUR begins to decline.

This method may be practiced with the MC.6 medium

A method of preparing OMPC which comprises culturing *Neisseria meningitidis* according above described method and subsequently isolating the outer membrane protein complex of the *Neisseria meningitidis*. In one embodiment this method is applied to the culture of *Neisseria meningitidis* is strain B11.

The foregoing description teaches generally how to ferment *Neisseria meningitidis* in a novel, defined medium to produce OMPC. The following examples are provided to teach more particularly how this invention may be carried out. However, the invention should not be construed as being limited to the specifics of the examples.

EXAMPLE 1

Bacterial strain

*N. meningitidis* B 11 (group B, serotype 2, see Gotschlich, E. C., Liu, T. Y., and Artenstein, M. S. Human immunity to the meningococcus III preparation and immunochemical properties of time group A, group B, and group C meningococal polysaccharides. *J. Exp. Med.* 129:1349–1365, 1969). U.S. Pat. No. 4,695,624 herein incorporated by reference was derived from a clinical isolate (M. Artenstein, Walter Reed Army Institute of Research, Washington, D.C.) which was cultured in the laboratory for tour passages prior to clonal isolation for Master Seed preparation. The Working Seed used in this study was generated from a Master Seed expansion. The strain was acclimated in MC.6 seed flask medium and cultured in the same medium to $OD_{600}$=3–4 prior to cryopreservation at –70° C. with 17% (w/v) glycerol. Strains of *N. meningitidis* B are on deposit with the ATCC (see #'s 13090–13094, 13096, 13098, 13100, 23247, 23249–23251, 23253–23255, 23583, 33086, 53044, ATCC Catalog of Bacteria and Bacteriophage, 17th edition, 1989, page 151). We have confirmed that *Neisseria meningitidis* ATCC reference strains of serogroups A, B, and C all grow on MC.6 agar. These additional serotypes of *Neisseria meningitidis* are also on deposit with the ATCC (see above reference, page 151, #35558, 13077, 13102, 13103, 13105–13112, 23248, 23252, 31275). Thus, with some adaptation by streaking on solid media and selection of vigorously growing colonies, it is predictable that any of these strains of Neisseria, including related microorganisms, could be grown on the MC.6 medium.

EXAMPLE 2

Media

The medium for both flask and fermenter culture was the same, with the exception of a 100 mM HEPES (N-[2-hydroxyethyl]piperazine-N' -[2-ethanesulfonic acid]) supplement in the flask cultures used to enhance pH buffering capacity at pH 7. The medium, MC.6, is described above. All chemicals were reagent grade or better. Antifoam was added to medium for the fermenters at 0.50 mL/L (UCON LB-625, Union Carbide).

EXAMPLE 3

Fermentation 250-mL and 2-L seed flasks, containing 100 mL and 500 mL working volumes, were incubated in a shaker/incubator at 37±1° C. at 250 RPM (¾" throw) (PsycroTherm™, New Brunswick Scientific). To start a fermentation, the 250-mL flask was inoculated with 2 mL of rapidly thawed frozen culture. During cultivation of the 250-mL flask the incubator chamber was filled with a 5% $CO_2$/air mixture to stimulate growth initiation. When the $OD_{600}$ of a seed culture reached 1–2, a 5% transfer volume was used to inoculate the next seed stage (e.g., 2-L, flask, 15-L fermenter, 250-L fermenter). The 15-L seed fermenter (Micros™, New Brunswick Scientific) has a 10 L working volume and was operated at 37±1° C., 0.25 vvm air sparge, 3.5 psig vessel pressure, and 196 rpm (3×3.75 in Rushton impellers). The 250-L production fermenter (Fermatron™, New Brunswick Scientific) has a 200 L working volume and was operated at 37±1° C., 0.25 vvm air sparge, 3.5 psig vessel pressure, 97 rpm (3×7.56 in Rushton impellers). Both fermenters were operated at constant pH (set-point 7.0) using 10N NaOH or 9N $H_3PO_4$ for acid or base adjustment, and under agitation cascade control (dissolved oxygen set-point 30% of air saturation). Exhaust-gas composition ($CO_2$, $O_2$, and $N_2$) was monitored in both fermenters by mass spectrometry (MGA-1200, Perkin-Elmer). All work was carried out under NIH BL-2-LS conditions.

EXAMPLE 4

Assays

The optical density of the culture ($OD_{600}$) was determined at 600 nm (model 601, Milton Roy) in 1 cm light path cuvettes; samples were diluted below 0.3 OD units to fit the linear range of the spectrophotometer. Dry cell weight was measured by separately drying 5–10 mL of whole broth and cell-free broth (0.22 μm filtrate) in aluminum weighing pans, both in duplicate, at 80° C. for 48 hours or more. The filtrate weight was used to blank the whole broth weight; the volume displaced by the cells (1%) was considered negligible. Total carbon, hydrogen, and nitrogen elemental analyses were determined by combustion of a lyophilized washed pellet (mid-exponential phase growth) (Leco CHN 800 Determinator, Galbraith Laboratories). Total particle counts were measured electronically using a Coulter counter with a 30 μm aperture (model $Z_{BI}$, Coulter Electronics). Plated cell counts were determined by serial dilution of culture in PBS and plating on Mueller Hinton agar in triplicate. Plates were incubated at 37° C. for 48 hours in a 5% $CO_2$/air environment. Plates containing between 20 and 200 colonies per plate were enumerated and viable cell counts were expressed as colony forming units (CFU)/mL of culture.

The following analytes from cell-free broth (0.22 μm filtrates) samples were assayed. Free amino acids were measured on a Beckman 6300 amino acid analyzer using post-column derivitization with ninhydrin. Separation of amino acids was accomplished by strong cation exchange with gradient elution. Primary amino acids were monitored at 570 and 440 nm for secondary amines (proline channel). L-cysteine could not be reproducibly quantified by this method. Analysis of organic acids was accomplished by isocratic liquid chromatography using a BioRad Aminex ion exclusion analytical column followed by UV detection at 210 nm. A 8.9 mN sulfuric acid eluent (0.6 mL/min) was used with a total run time of 25 min. The standard curve range was 100 to 500 μg/mL for acetic, formic, pyruvic, lactic, and succinic acids. Cation analysis was performed by isocratic cation exchange chromatography (IonPac CS12, Dionex). The eluent was 20 mM methane sulfonic acid (1.0 mL/min) and analytes were detected by conductivity (range 30). The total run time was 20 min. Standard curve range was 0.5 to 25 μg/mL for potassium and sodium ions, and 1 to 50 μg/mL for ammonium, calcium, and magnesium ions. The glucose concentration in the broth was determined using the Beckman Glucose Analyzer 2 (glucose oxidase reaction).

EXAMPLE 5

Fermentation Productivity Comparison of the Defined Medium OMPC Fermentation Process with the yeast Extract OMPC Fermentation Described in Marburg, et al., U.S. Pat. No. 4,695,624

The following data demonstrates that the defined medium process described in this patent disclosure is more consistent and generates higher final cell yields (based on three independent methods of quantification) than a yeast extract based fermentation process. The yeast extract fermentation process was scaled-down (from 800-L to 16-L) for the generation of this data; data for the defined medium fermentation process was obtained at the 250-L scale. Different lots of yeast extract were evaluated for this comparison to illustrate the variability of the yeast extract fermentation process:

| Fermentation Lot # | $OD_{600}$ | Total cell count (particles/ml) | Dry cell weight (g/L) |
|---|---|---|---|
| yeast extract 1 | 3.7 | $3.2 \times 10^9$ | — |
| yeast extract 2 | 1.9 | $1.8 \times 10^9$ | — |
| yeast extract 3 | 2.1 | $3.1 \times 10^9$ | — |
| yeast extract 4 | 4.3 | $3.4 \times 10^9$ | — |
| yeast extract 5 | 4.2 | — | — |
| yeast extract 6 | 5.7 | — | 2.27 |
| defined medium 1 | 12 | $1.3 \times 10^{10}$ | — |
| defined medium 2 | 12 | $1.3 \times 10^{10}$ | — |
| defined medium 3 | 13 | $1.4 \times 10^{10}$ | 4.92 |

These data clearly show the reproducibility of the process claimed herein as compared with the variability, but consistently lower productivity, of a yeast-extract based fermentation process for Neisseria fermentation.

EXAMPLE 6

Conjugation of Polysaccharide to OMPC Isolated From Neisseria Meningitidis B11 Cultured According to this Invention, and Immunogenicity of the Conjugate Analytical data of conjugates of Haemophilus influenzae b capsular polysaccharide (polyribosyl ribitol phosphate, PRP) and OMPC derived from the instant fermentation process. Methods for PRP production and conjugation with OMPC are described in U.S. Pat. No. 4,695,624 and are herein incorporated by reference for this purpose:

| Test | Test Limit | Conjugation[i] |
|---|---|---|
| SCMHC/Lys | ≧0.01 | 0.05 |
| SCMC/Lys | ≧0.01 | 0.02 |
| SCMHC/$PRP_m$ | ≦0.25 | 0.12 |
| SCMHC + SCMC/$PRP_m$ | ≦0.30 | 0.17 |
| SCMHC + SCMC/$BuA_2$ | 0.83–1.33 | 0.83 |
| Polysaccharide | μg/mL | 133.3 |
| Protein | μg/mL | 2572.7 |
| Antigen | μg/mL | 115.7 |
| Polysac/Protein | 0.05–0.1 | 0.05 |
| Antigen/Polysac | — | 0.87 |
| Blood group substance | * | pass |
| Molecular sizing | ≧85% < $K_d$ 0.25 | 85.3% |

[i]0.1M phosphate reaction, pH 8.0, see U. S. Pat. No. 4,695,624
*Type A < 4 μg/BGS μgPolysac/mL;
Type B < 80 μg/BGS μgPolysac/mL Definitions:

| | |
|---|---|
| SCMHC | S-(carboxymethyl)homocysteine |
| SCMC | S-(carboxymethyl)cysteamine |
| BuA | 1,4-butanediamine |
| $K_d$ | molecular weight distribution |
| Lys | lysine |

SCMHC, a hydrolitically stable and assayable acid hydrolysis product of the bigeneric spacer, is used as a measure of covalency of the conjugated PRP-OMPC product. SCMC is a hydrolitically stable and assayable acid hydrolysis product of the derivitized PRP capping agent, required to terminate excess alkylating sites on unconjugated PRP-$BuA_2$-BrAc. Ratios of SCMHC and SCMC to a standard internal to the conjugate (e.g., lysine) measurably greater than 0 substantiates the efficiency of the covalent bond between PRP and OMPC, or capping reagent, respectively. The various ratios of SCMHC and SCMC to PRP and $BuA_2$ (an assayable moiety of the derivitized PRP spacer), along with the polysaccharide, protein, and antigen ratios and $K_d$, define and demonstrate consistency of the conjugated product. The data obtained for the conjugation parameters outlined in U.S. Pat. No. 4,695,624 provide evidence to support the usefulness of the process disclosed and claimed herein to produce OMPC which can be conjugated to polysaccharide.

These data demonstrate that the OMPC produced from Neisseria according to the instant invention conjugates with PRP in the expected manner. The polysaccharide loading and antigenicity of the conjugate is also at least as good as conjugation data reported in the U.S. Pat. No. 4,695,624 patent using the OMPC produced from yeast extract based fermentations. The polysaccharide loading and antigenicity of the conjugate is also at least as good as conjugation data reported in the U.S. Pat. No. 4,695,624 patent using yeast extract based Neisseria fermentation for production of OMPC (see below).

EXAMPLE 7

Immunogenicity of Conjugates Prepared with OMPC Produced From Neisseria Cultured According to this Invention Two month old Rhesus monkeys were immunized with the doses of conjugated OMPC-PRP as indicated in the tables below on days 0 and 28. Sera collected on days 0, 28, and 42 were assayed for antibodies to *Haemophilus influenzae* PRP by radioimmunoassay.

TABLE I

INFANT RHESUS MONKEY IMMUNOGENICITY

| Dose μg | Monkey # | RIA Titer, μg anti-PRP/mL | | |
|---|---|---|---|---|
| | | Day 0 | Day 28 | Day 42 |
| | | | Individual animal | |
| 1 | 28039 | <0.1 | 0.7 | 0.5 |
| | 28057 | Died | | |
| | 28061 | <0.1 | 15.2 | 209 |
| | | | GMT | |
| | | <0.1 | 2.1 | 10.2 |
| | | | Individual animal | |
| 0.1 | 28235 | <0.1 | 1.3 | 12.2 |
| | 28236 | <0.1 | 0.7 | 19.9 |
| | 28237 | <0.1 | 4.2 | 135.6 |
| | | | GMT | |
| | | <0.1 | 1.6 | 32.1 |

These data show that the vaccine prepared with OMPC produced from Neisseria cultured according to this invention and conjugated as described above (see Example 6) is fully immunogenic. Furthermore, the vaccine prepared with this OMPC and conjugated as described in U.S. Pat. No. 4,695,624 has immunogenicity at a dose of 0.010 μg, which is similar to the immunogenicity of thimerosal-free, liquid PedvaxHIB®. The immunogenicity of PedvaxHIB® can range from 0.2 to 156 μg/mL after dose 1 and from 8.1 to 456 μg/mL after dose 2. In the past, immune responses within these limits in subhuman primates has correlated with protective efficacy of PedvaxHIB® in man. Thus, conjugation of OMPC produced from Neisseria cultured according to this invention and conjugated with polysaccharide results in an immunogenic product.

What is claimed is:

1. A defined medium, named MC.6, which comprises, (±10%) the following components (mg/L):

| Component | MC.6 |
|---|---|
| NaCl | 5800 |
| K₂HPO₄ | 4000 |
| NH₄Cl | 1000 |
| K₂SO₄ | 1000 |
| Glucose | 10000 |
| L-Glutamic Acid | 3900 |
| L-Arginine | 150 |
| Glycine | 250 |
| L-Serine | 500 |
| L-Cysteine.HCl | 100 |
| MgCl₂.6H₂O | 400 |
| CaCl₂.2H₂O | 28 |
| Fe(III) Citrate | 40. |

2. A method for culturing *Neisseria meningitidis* cells to an optical density of about 10–13 at 600 nm, which comprises culturing *Neisseria meningitidis* cells in a medium containing only the five amino acids Glu, Arg, Gly, Ser and Cys, salts and a carbon source, and harvesting the cells in late log or early stationary phase.

3. The method of claim 2 which comprises the steps of:
(a) preparing a frozen seed inoculum of *Neisseria meningitidis* in a medium containing only the five amino acids Glu, Arg, Gly, Ser and Cys, salts, a carbon source, buffered to maintain a pH of about 7, and a cryoprotective agent;

(b) preparing a seed inoculum in the same medium used in Step(a) but buffered to maintain a pH of about 7, using about a 1/100th volume of the frozen seed inoculum of Step(a) to initiate growth, and growing the *Neisseria meningitidis* to an optical density at 600 nm of about 1–2 in an atmosphere of about 5% $CO_2$;

(c) transferring the seed inoculum of Step(b) into a volume of the same medium used in Step(b) equal to about 10–100 fold the volume of the seed inoculum and growing this culture to an optical density of about 1–2 at 600 nm;

(d) inoculating a fermentation vessel containing about 10–100 fold the volume of the same medium as in the culture of Step 9(c), without addition of buffer, and culturing the *Neisseria meningitidis* with addition of acid or base as needed to maintain the pH at about 7, and supplying sufficient dissolved oxygen to maintain exponential growth as measured by carbon dioxide evolution rate (CER) and oxygen uptake rate (OUR);

(e) optionally, inoculating a fermentation vessel containing about 10–100 fold the volume of the same medium as in the culture of Step 9(c), without addition of buffer, and culturing the *Neisseria meningitidis* with addition of acid or base as needed to maintain the pH at about 7, and supplying sufficient dissolved oxygen to maintain exponential growth as measured by carbon dioxide evolution rate (CER) and oxygen uptake rate (OUR); and (f) harvesting the *Neisseria meningitidis* of Step(d) at the point where the CER and OUR begins to decline.

4. The method of claim 3 wherein the medium contains the following components (mg/L):

| Component | Amount (mg/L) |
|---|---|
| NaCl | 5800 |
| K₂HPO₄ | 4000 |
| NH₄Cl | 1000 |
| K₂SO₄ | 1000 |
| Glucose | 10000 |
| L-Glutamic Acid | 3900 |
| L-Arginine | 150 |
| Glycine | 250 |
| L-Serine | 500 |
| L-Cysteine.HCl | 100 |
| MgCl₂.6H₂O | 400 |
| CaCl₂.2H₂O | 28 |
| FE(III) Citrate | 40 |

5. A method of preparing outer membrane protein complex OMPC which comprises culturing *Neisseria meningitidis* according to the method of claim 4 and subsequently isolating the outer membrane protein complex of the *Neisseria meningitidis*.

6. The method of claim 5 wherein the *Neisseria meningitidis* is strain B11.

7. A method of fermenting *Neisseria meningitidis* comprising culturing *N. meningitidis* in the medium of claim 1.

* * * * *